United States Patent
Wang et al.

(10) Patent No.: US 10,314,486 B2
(45) Date of Patent: Jun. 11, 2019

(54) HEAD-MOUNTED INDIRECT OPTHALMOSCOPE CAMERA

(71) Applicant: THE JOHNS HOPKINS UNIVERSITY, Baltimore, MD (US)

(72) Inventors: Aaron Wang, Cupertino, CA (US); John Avallone, Annapolis, MD (US); David Guyton, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 173 days.

(21) Appl. No.: 15/502,565

(22) PCT Filed: Jun. 18, 2015

(86) PCT No.: PCT/US2015/036394
§ 371 (c)(1),
(2) Date: Feb. 8, 2017

(87) PCT Pub. No.: WO2016/022215
PCT Pub. Date: Feb. 11, 2016

(65) Prior Publication Data
US 2018/0206720 A1    Jul. 26, 2018

Related U.S. Application Data

(60) Provisional application No. 62/034,828, filed on Aug. 8, 2014.

(51) Int. Cl.
*A61B 3/10* (2006.01)
*A61B 3/12* (2006.01)
(Continued)

(52) U.S. Cl.
CPC .............. *A61B 3/12* (2013.01); *A61B 3/0008* (2013.01); *A61B 3/0033* (2013.01);
(Continued)

(58) Field of Classification Search
CPC ........... A61B 3/12; A61B 3/14; A61B 3/0033; A61B 3/0008; A61B 3/0083;
(Continued)

(56) References Cited

U.S. PATENT DOCUMENTS 5,841,509 A * 11/1998 Harooni ................ A61B 3/132
                                                          351/221
6,089,716 A     7/2000 Lashkari et al.
(Continued)

FOREIGN PATENT DOCUMENTS

WO       2011042722 A1    4/2011

OTHER PUBLICATIONS

Shanmugam, M., "Video Indirect Ophthalmoscopy Using a Hand-Held Video Camera" Indian J Opthalmol (2011) vol. 59, No. 1, pp. 53-55.
(Continued)

*Primary Examiner* — William R Alexander
*Assistant Examiner* — Henry A Duong
(74) *Attorney, Agent, or Firm* — Harrity & Harrity, LLP

(57) ABSTRACT

The present invention is directed to an indirect ophthalmoscopic system for imaging of the ocular fundus including a headband configured to hold a digital imaging device and a plus eyepiece lens in front of an eye of the examiner, with the plus eyepiece lens positioned in between the digital imaging device and the examiner's eye, such that the examiner is focused upon the display of the digital imaging device. The aperture of the digital imaging device receives light reflected from the ocular fundus of the patient's eye, emanating from the patient's pupil. The examiner examines the patient and composes the image of the ocular fundus directly in the display screen. In this way, what the examiner sees is captured by the digital imaging device. Stereoscopic imagery is obtained by optical means that create side-by-
(Continued)

side virtual images of the aperture of the digital imaging device within the pupil of the eye.

21 Claims, 7 Drawing Sheets

(51) Int. Cl.
*A61B 3/00* (2006.01)
*H04N 13/207* (2018.01)
*H04N 13/339* (2018.01)
*A61B 3/14* (2006.01)
*A61B 90/50* (2016.01)

(52) U.S. Cl.
CPC .............. *A61B 3/0083* (2013.01); *A61B 3/14* (2013.01); *H04N 13/207* (2018.05); *H04N 13/339* (2018.05); *A61B 2090/502* (2016.02)

(58) Field of Classification Search
CPC . A61B 2090/502; A61B 3/145; A61B 3/1225; A61B 3/102; H04N 13/207; H04N 13/339

USPC ........................................................ 351/206
See application file for complete search history.

(56) References Cited

U.S. PATENT DOCUMENTS

| | | |
|---|---|---|
| 2002/0060778 A1* | 5/2002 | Su .......................... A61F 9/008 351/206 |
| 2005/0110949 A1 | 5/2005 | Goldfain |
| 2007/0070294 A1 | 3/2007 | Kim |
| 2012/0162604 A1 | 6/2012 | Nussenbaum |
| 2013/0083185 A1 | 4/2013 | Coleman, III |

OTHER PUBLICATIONS

Bastawrous, A., "Smartphone Fundoscopy" (2012) Ophthalmology, 119 (2) 432-433.

* cited by examiner

Infant fundus.

Normal adult fundus.

Cotton wool spot.

Fungus seeding.

Large choroidal nevus.

Traumatic subretinal heme.

HEAD-MOUNTED INDIRECT OPTHALMOSCOPE CAMERA

CROSS-REFERENCE TO RELATED APPLICATIONS

This application is a 35 U.S.C. § 371 U.S. national entry of International Application PCT/US2015/036394, having an international filing date of Jun. 18, 2015, which claims the benefit of U.S. Provisional Application No. 62/034,828, filed Aug. 8, 2014, the content of each of the aforementioned applications is herein incorporated by reference in their entirety.

FIELD OF THE INVENTION

The present invention relates generally to medical devices. More particularly, the present invention relates to a system and method for imaging the ocular fundus and screening for eye diseases.

BACKGROUND OF THE INVENTION

Ocular fundus imaging is used to examine and record images of internal structures in the back the eye (the ocular fundus), including structures such as the retina, optic disc, macula, and posterior pole. Fundus imaging can be used to detect and monitor diseases that affect the eye. Conventional table-top fundus imaging devices are impractical for some patients, such as infants, young children, and bedridden patients who cannot hold still or maneuver into the necessary position for proper eye alignment with the camera. Many portable hand-held fundus cameras are very expensive and are difficult or awkward to use. A hand-held camera can be used in an indirect ophthalmoscope arrangement but still needs a condensing lens held in the other hand. This occupies both hands of the examiner, with manipulation of the lids or scleral depression by the second hand no longer being possible. In addition, most ophthalmologists are not accustomed to such a bi-manual camera aiming technique. A head-mounted indirect ophthalmoscope with an integrated camera is ideal, but existing such devices have flaws that affect image quality. For instance, one such existing head-mounted indirect ophthalmoscope with an integrated camera places the effective camera aperture between the effective apertures of the examiner's two pupils. Consequently, this indirect ophthalmoscope with an integrated camera can allow the examiner to obtain a good monocular view, but the instrument can be easily misaligned for the camera, causing vignetting and poor quality images. Also, stereoscopic imaging of the ocular fundus is not possible with existing head-mounted indirect ophthalmoscopes.

Accordingly, there is a need in the art for a fundus imaging device, using manipulation that is familiar to, and easily used by the ophthalmologist that provides reliable, quality images.

SUMMARY OF THE INVENTION

The foregoing needs are met, to a great extent, by the present invention which provides a system for imaging an ocular fundus including a digital imaging device having a display. The system also includes a light source, a condensing lens, and a plus eyepiece lens. A head mounting device for the digital imaging device, light source, and plus eyepiece lens is configured to hold the digital imaging device in front of an examiner's eye, such that the light source is positioned near an aperture of the digital imaging device, and such that the plus eyepiece lens is positioned between the examiner's eye and the display of the digital imaging device.

In accordance with an aspect of the present invention, the system for imaging includes the light source being integrated into the digital imaging device. The digital imaging device takes the form of a one selected from a group consisting of digital camera and smartphone. The digital imaging device takes the form of two digital imaging devices to provide three-dimensional imaging. A remote-controlled shutter can be used.

In accordance with another aspect of the present invention, a system for imaging an ocular fundus includes a digital imaging device having a display. The system also includes a light source, a condensing lens, and a plus eyepiece lens. A head mounting device for the digital imaging device, light source, and plus eyepiece lens is configured to hold the digital imaging device in front of an examiner's eye, such that the light source is positioned near an aperture of the digital imaging device, and such that the plus eyepiece lens is positioned between the examiner's eye and the display of the digital imaging device. A non-transitory computer readable medium is programmed for assisting in examination of a patient. The light source is integrated into the digital imaging device. The digital imaging device takes the form of a one selected from a group consisting of digital camera and smartphone. The digital imaging device takes the form of two digital imaging devices to provide three-dimensional imaging. A remote-controlled shutter can be used. The non-transitory computer readable medium is further programmed to provide functions chosen from among the following: activation of the shutter trigger, adjustment of the level and mode of illumination from the light source, auto-focus adjustment, image processing of the images obtained.

In accordance with yet another aspect of the present invention, a system for obtaining side-by-side stereoscopic images of an ocular fundus of a subject includes a light source and a digital imaging device having an aperture for receiving light reflected from the ocular fundus of said subject. The system includes an optical means for creating side-by-side virtual images of the aperture of said digital imaging device. the system also includes a condensing lens and a head-mounting device for head-mounted positioning of said light source, digital imaging device, and optical means. The positioning of said light source, digital imaging device, and optical means causes said light source and the light paths from said side-by-side virtual images to be imaged by said condensing lens to positions separated from one another within the pupil of the eye of said subject, such as to obtain stereoscopic views of the ocular fundus of the subject.

In accordance with still another aspect of the present invention, a display on the digital imaging device and two plus eyepiece lenses is positioned between the examiner's eyes and the stereoscopic images on the display for viewing of a binocularly fused stereoscopic view of the ocular fundus. Binocular electro-optical goggles can be included, which electronically receive the stereoscopic images obtained by said digital imaging device, for stereoscopic viewing by the examiner. The optical means, for creating side-by-side virtual images of the aperture of said digital imaging device, includes a prismatic means. The prismatic means can take the form of a biprism. The biprism includes an achromatic biprism for reduction of chromatic aberration. The optical means, for creating side-by-side virtual images of the aperture of said digital imaging device, includes reflecting means. The reflecting means include reflecting surfaces positioned to avoid tilting of the stereoscopic images of the ocular fundus with respect to one another. The reflecting means include reflecting surfaces chosen from a group consisting of mirrors and internally reflecting prisms. The optical means is positioned such that the light source emits a beam of light that is not occluded by said optical means.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to an indirect ophthalmoscopic system for imaging including a headband configured to hold a digital imaging device and a plus eyepiece lens in front of an eye of the examiner. The digital imaging device is positioned such that a display of the digital imaging device is positioned in front of an eye of the examiner. The plus eyepiece lens is positioned in front of the display, in between the digital imaging device and the examiner's eye, typically the examiner's dominant eye. The plus eyepiece lens, preferably achromatic, allows close-up viewing of the display by the examiner. For a young or highly nearsighted examiner who can already focus up close, the plus eyepiece lens can be removed or swung out of the way. The aperture of the digital imaging device defines the only observation path for viewing the fundus of the patient's eye. The examiner examines the patient using conventional exam techniques and composes the image directly in the display screen of the digital imaging device. In this way, what the examiner sees is what is captured by the digital imaging device. The digital imaging device can take the form of a digital camera with a display, a smartphone, or other similar device. It is advantageous if the digital imaging device includes a light source near its aperture, such as a light-emitting diode (LED), which placement allows the condensing lens to form an image of the aperture and the light source adjacent to each other in the pupil of the patient's eye, accomplishing Gullstrand's "reflex-free principle" of indirect ophthalmoscopy. A remote-controlled shutter can also be included in order to allow the examiner to operate the system in a hands-free manner.

Figure 1:
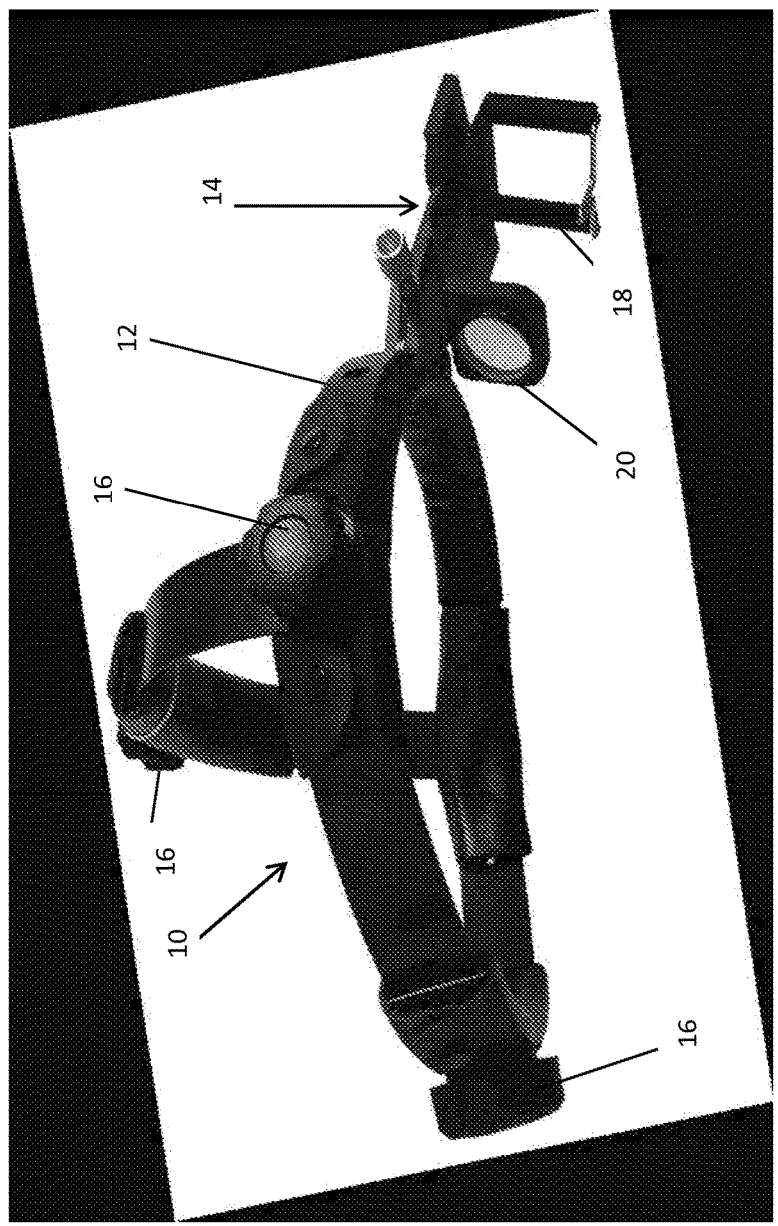
FIG. 1 illustrates a head-mounted device used in imaging a fundus of a patient's eye, according to an embodiment of the present invention.

FIG. 1 illustrates a device used in imaging a fundus of a patient's eye, according to an embodiment of the present invention. As illustrated in FIG. 1, the device 10 includes a headband 12 with mounting hardware 14. The headband 12 can also include size adjustment hardware 16. It should be noted that the headband 12 can take any suitable head mounting form known to or conceivable to one of skill in the art such as glasses, headbands, straps, or other headpieces. The mounting hardware 14 includes a digital imaging device holder 18 and a plus eyepiece lens holder 20. The digital imaging device holder 18 is positioned such that a display of the digital imaging device is positioned in front of an eye of the examiner. Preferably, the digital imaging device is positioned in front of a dominant eye of the examiner. The plus eyepiece lens holder 20 is positioned between the digital imaging device holder 18 and the eye of the examiner, such that the plus eyepiece lens allows close-up viewing by the examiner of the display of the digital imaging device by relaxing, or substituting for, the examiner's accommodation. The lens can be easily removed or swung out of the way if a young or nearsighted examiner prefers not to use it. As arranged in FIGS. 1, 2A, and 2B, the aperture of the digital imaging device acts as the only observation path for the rays of light emanating back from the patient's fundus. The examiner aligns the instrument with the patient's eye and composes the image directly in the display screen, before taking an image or a series of images. In this way, what the examiner sees is what is captured by the digital imaging device.

The digital imaging device can take the form of a digital camera with a display, a smartphone, a tablet, a phablet, or other similar device known to or conceivable to one of skill in the art. The smart device's native camera and light are used to record the exam. Other possible devices are Google Glass or action cameras like GoPro, but they would require an external light source. The method of the present invention can also be accomplished with two head-mounted cameras to create stereoscopic viewing and recording. It is advantageous if the digital imaging device includes an integrated light source, such as a flash or LED. A remote-controlled shutter can also be included in order to allow the examiner to operate the system in a hands-free manner.

In contrast to conventional head-mounted indirect ophthalmoscopes, the headset of the present invention typically does not include the camera optics, light source, or power source, because these elements are supplied by the digital imaging device itself. The imaging system of the present invention allows a medical examiner to perform the indirect ophthalmoscopic exam in virtually the same fashion as when using a conventional head-mounted indirect ophthalmoscope. One hand holds the condensing lens, and the other hand is free and not awkwardly holding the camera. With one hand free, the examiner is able to aid in opening the patient's eyelids or perform scleral depression during the examination.

Figure 2A:
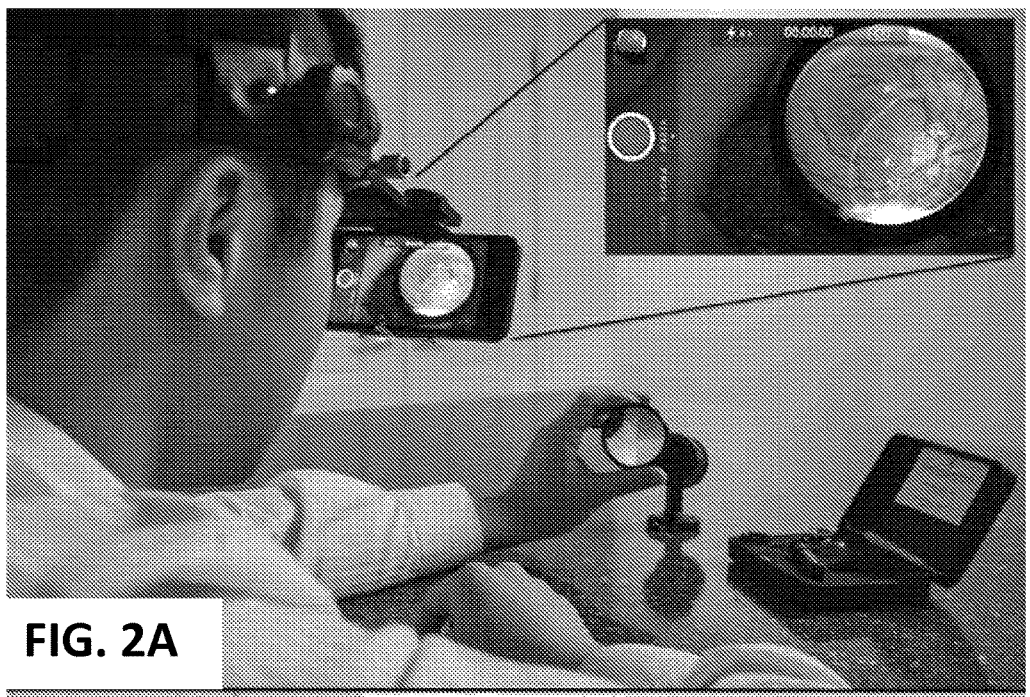
FIGS. 2A and 2B illustrate an exemplary implementation of the present invention for imaging of the fundus.
Figure 2B:
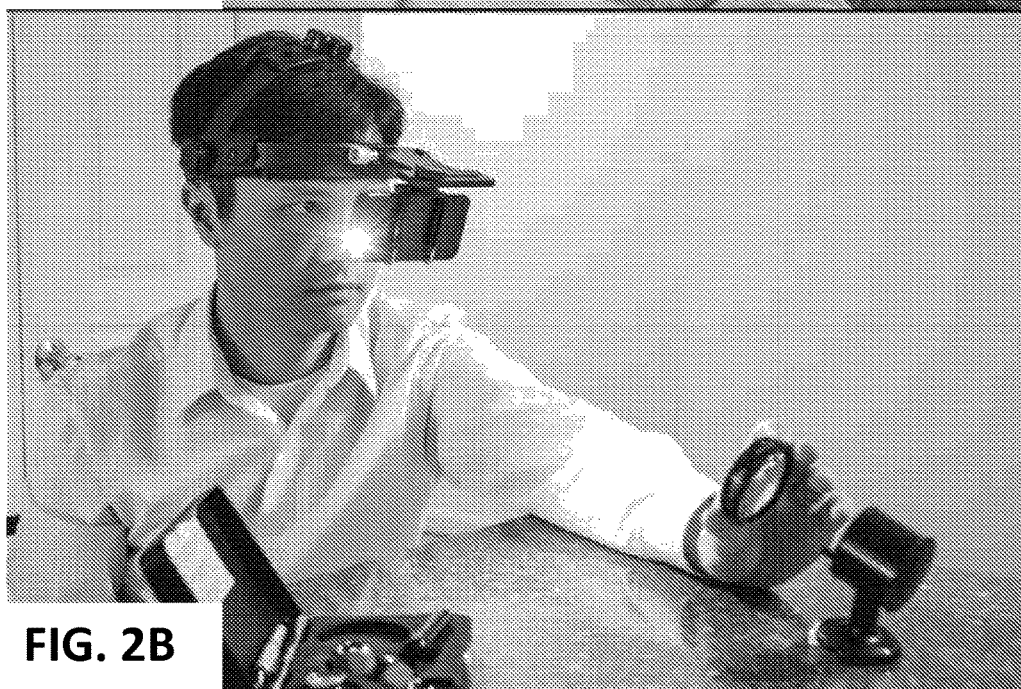

FIGS. 2A and 2B illustrate an exemplary implementation of the present invention for imaging of the fundus. The system includes the headband, mounting hardware, smartphone camera with display and LED, a plus eyepiece lens, and a condensing lens. In practice, the camera is mounted with the LED positioned near and preferably above the aperture, as is the case for the light source with conventional indirect ophthalmoscopes. The condensing lens is positioned in front of the patient's pupil, where it is hand-adjusted during use to image both the camera aperture and the LED within the pupil of the patient's eye. The camera can be set to take still shots or video images of the fundus. The LED can be set for continuous illumination. The camera's shutter button, or a remote foot-activated switch, or a stop/start switch, can be used to engage the imaging function of the camera. In addition, others behind the examiner can see what the examiner is seeing on the display of the imaging device, which makes the instrument ideal for teaching purposes.

Figure 3A:
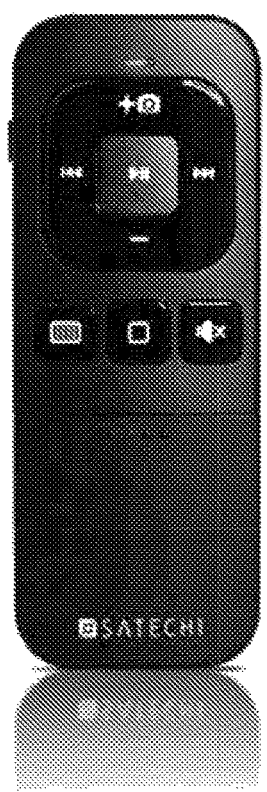
FIGS. 3A and 3B illustrate a remote control for a shutter, according to an embodiment of the present invention.
Figure 3B:
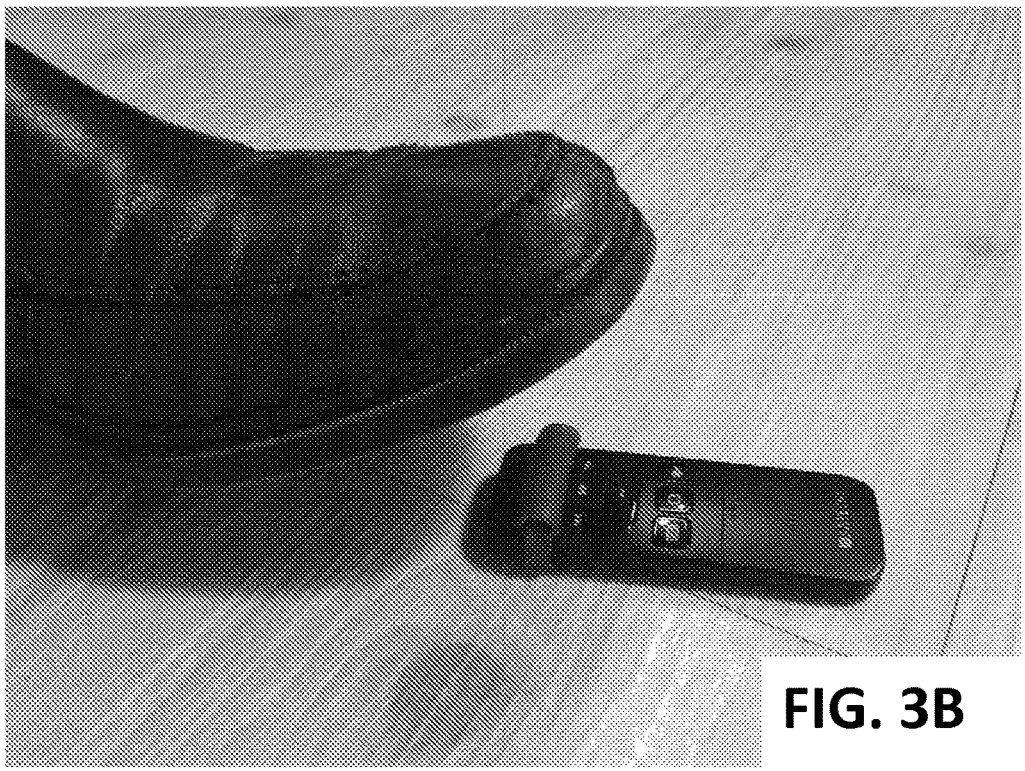

FIGS. 3A and 3B illustrate a remote control for a shutter, according to an embodiment of the present invention. FIG. 3A illustrates a typical wireless remote control for a shutter. This remote control can be configured in a number of other forms, such as a conventional foot switch, or a switch attached to the condensing lens that can be triggered by the same hand holding the condensing lens.

As illustrated in FIG. 3B, the remote control for the shutter of FIG. 3A can be converted into a foot-activated switch with a small portion of rubber tubing. Any other suitable remote control for the shutter could also be used (for example converted into a foot-activated remote control), or a dedicated foot switch could be used to trigger the shutter remotely.

Figure 4A:
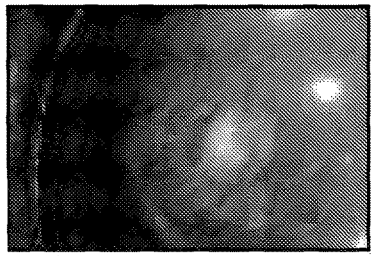
FIGS. 4A-4F illustrate exemplary images obtained using a system according to an embodiment of the present invention.
Figure 4D:
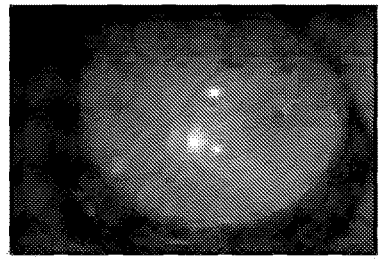
Figure 4B:
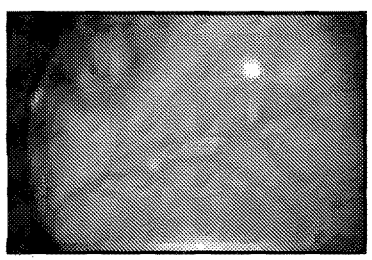
Figure 4E:
Figure 4C:
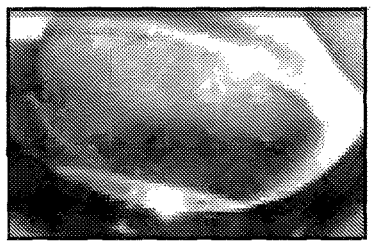
Figure 4F:

FIGS. 4A-4F illustrate exemplary images obtained using a system according to an embodiment of the present invention. The system preserves the familiar indirect ophthalmoscopic exam technique. This allows for head positioning and manipulation of the condensing lens to reduce glare. The system also allows for one free hand to hold open eyelids or to perform scleral depression. FIG. 4A shows an image of an infant's fundus. FIG. 4B shows an image of a cotton wool spot. FIG. 4C shows an image of a large choroidal nevus. FIG. 4D shows an image of a normal adult fundus. FIG. 4E shows an image of fungus seeding, and FIG. 4F shows an image of traumatic subretinal blood. All of these images were obtained according to an embodiment of the present invention.

Figure 5:
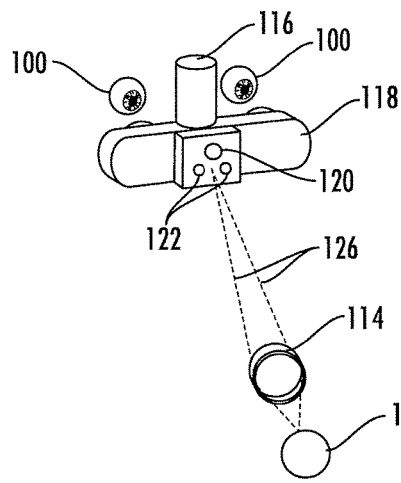
FIGS. 5 and 6 illustrate a perspective view and a top-down view of a typical prior-art head-mounted binocular indirect ophthalmoscope.
Figure 6:
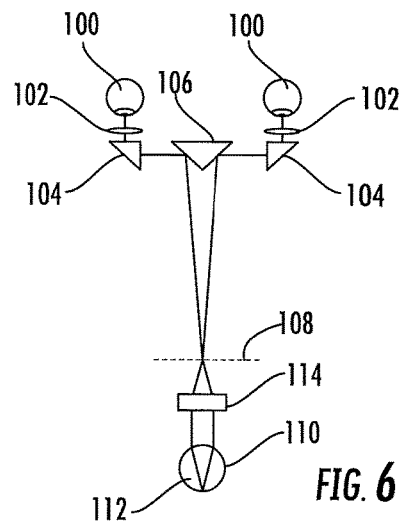

FIGS. 5 and 6 illustrate a typical prior-art head-mounted binocular indirect ophthalmoscope. Both eyes 100 of the examiner view through plus eyepiece lenses 102, into reflecting prisms 104, and then off reflecting prism 106, to view aerial image 108 of the fundus 112 of patient's eye 110. An aerial image 108 of the illuminated fundus 112 of patient's eye 110 is formed by condensing lens 114 into a position approximately 1 to 12 centimeters on the other side of condensing lens 114 from patient's eye 110, with this distance depending upon the refractive error of patient's eye 110.

Figure 7:
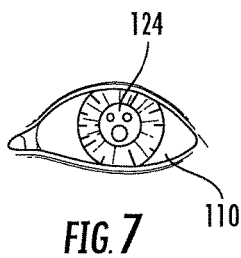
FIG. 7 illustrates a front view of an eye of a subject depicting the placement of the beams of light according to the systems illustrated in FIGS. 5 and 6.

As illustrated in FIGS. 5 and 6, a light source contained within enclosure 116 is reflected by a 45° mirror (not shown) contained within enclosure 118 to emerge from enclosure 118 through aperture 120. The separation of the viewing paths of the examiner's eyes 100 is reduced by prisms 104 and 106 approximately four-fold, from a distance of approximately 60 mm to a distance of approximately 15 mm, with these viewing paths emerging from enclosure 118 through apertures 122. Apertures 122 and aperture 120 are grouped close together but are non-overlapping, such that these apertures are imaged by condensing lens 114 onto the cornea of patient's eye 110, fitting within pupil 124 of patient's eye 110, as illustrated by dotted construction lines 126 in FIG. 5 and by images of apertures 122 and 120 drawn within the pupil 124 of eye 110 in FIG. 7. Imaging of apertures 122 and 120 onto the cornea of patient's eye 110 satisfies the Gullstrand principle of reflex-free indirect ophthalmoscopy, because if the illumination light passes through the cornea at a different position on the cornea from where the observation pathways pass through the cornea, the illumination light cannot be reflected back into the examiner's eyes from the cornea, avoiding washing out of the examiner's view of the fundus 112 of patient's eye 110.

In FIGS. 5 and 6, because the examiner's eyes 100 view aerial image 108 from offset but converging directions, the examiner can appreciate a stereoscopic image of aerial image 108, the basis of stereoscopic binocular indirect ophthalmoscopy.

Figure 8:
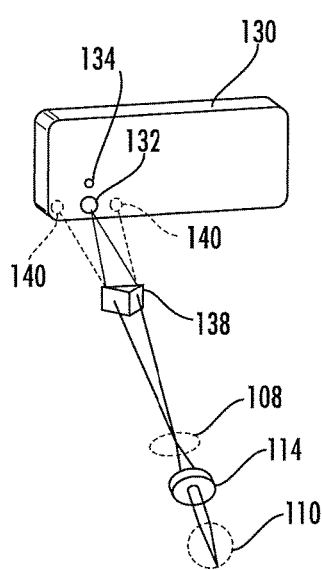
FIGS. 8 and 9 illustrate perspective views of one embodiment of the present invention, an attachment to a head-mounted indirect ophthalmoscope camera.
Figure 9:
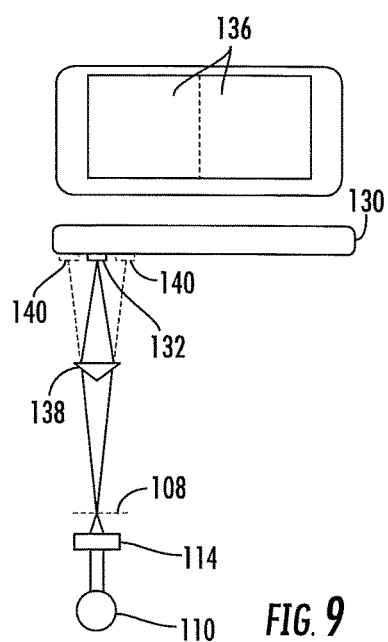
Figure 10:
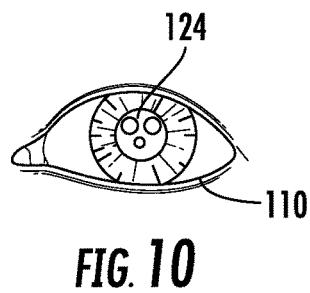
FIG. 10 illustrates a front view of an eye of a subject depicting the placement of the beams of light according to the systems illustrated in FIGS. 8 and 9.

FIGS. 8 and 9 illustrate one embodiment of the present invention, an attachment to a head-mounted indirect ophthalmoscope camera, for example smart phone 130, with enclosed camera having aperture 132. While a smartphone is used herein as an example, any suitable device that can take images that are displayed either on an incorporated display screen or that may be routed to separate electro-optical goggles for stereoscopic viewing, known to or conceivable by one of skill in the art, could also be used for the implementation of the present invention. The light source 134 for the enclosed camera is typically a small white LED, located close to, but not overlapping, the camera aperture 132. It should be noted that the light source can take any form known to or conceivable by one of skill in the art. For the digital camera to obtain and display side-by-side stereoscopic images 136 of aerial image 108, two virtual images of aperture 132 are produced by optical means to view aerial image 108 from offset but converging directions. This is accomplished in FIGS. 8 and 9 by biprism 138, producing side-by-side virtual images 140 of camera aperture 132. By proper choice of dimensions and positioning of biprism 138, virtual images 140 of camera aperture 132 will be located close to, but not overlapping, camera aperture 132 and light source 134. Virtual camera apertures 140 and light source 134 are imaged by condensing lens 114 onto the cornea of patient's eye 110, fitting within pupil 124 of patient's eye 110, as illustrated in FIG. 10. This arrangement allows both viewing paths from virtual camera apertures 140 to fit within pupil 124, separated from the illuminating light path from light source 134, providing the production of stereoscopic images 136 of aerial image 108. Side-by-side stereoscopic images 136 are viewed by the examiner through bilateral close-up eyepiece lenses, not shown, providing 3D viewing of aerial image 108. Alternatively, the stereoscopic images may be routed to separate electro-optical goggles for stereoscopic viewing. The biprism 138 can be attached to smartphone 130 or to the wearable headpiece such that it is positioned correctly for producing the side-by-side virtual images of camera aperture 132. The biprism 138 is also attached to smartphone 130 or to the head-mounted unit in such a way as to allow light from light source 134 to pass above the biprism 138.

Figure 11:
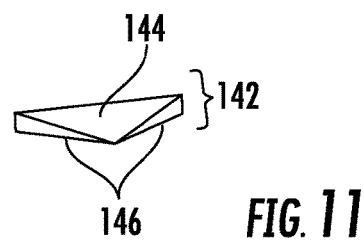
FIG. 11 illustrates a cross-sectional view of a prism according to the embodiment of the present invention illustrated in FIGS. 8 and 9.

Chromatic aberration introduced by biprism 138 can degrade the quality of stereoscopic images 136. Such image degradation can be avoided by substituting achromatic biprism 142 (illustrated in FIG. 11) for biprism 138. The achromatic biprism 142 illustrated in cross section in FIG. 11 is comprised of lower-index biprism 144 supporting two cemented higher-index prisms 146 to help neutralize chromatic aberration as is well known in the art.

An advantage of the apparatus shown in FIGS. 8 and 9 is that the entire camera aperture 132 is used to obtain each of the stereoscopic images 136. Other single-camera stereoscopic imaging devices known to the art use only one half of the camera aperture for each of the stereoscopic images, introducing aberrations and reducing resolution. A design constraint of the apparatus shown in FIGS. 8 and 9 is that biprism 138 must be small enough to allow the illuminating light from light source 134 to pass above biprism 138 to be captured by condensing lens 114 and thereby be directed to the cornea and pupil of eye 110.

Figure 12:
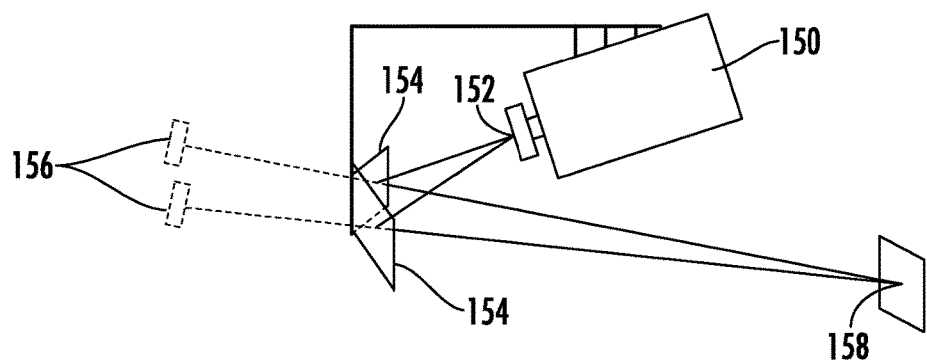
FIG. 12 illustrates a prior art reflecting apparatus.

FIG. 12 illustrates a prior art reflecting apparatus. Camera aperture 152 of camera 150 is reflected by tilted mirrors 154 to produce virtual images 156 of camera aperture 152, which are offset from one another and whose light paths are converging toward scene 158, producing side-by side stereoscopic images by camera 150 of scene 158. A disadvantage of such reflecting systems, however, is that oblique reflection from tilted mirrors practically always produces rotated (tilted) stereoscopic images which must be straightened by optical or image processing means for proper stereoscopic viewing.

Figure 13:
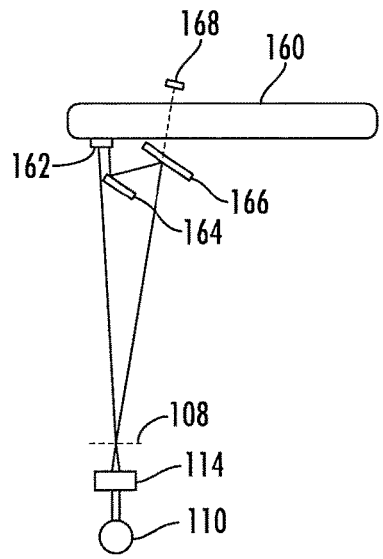
FIG. 13 illustrates prior art reflecting means for obtaining a single virtual image of half of the camera aperture of a smart phone, for the purpose of obtaining stereoscopic imaging in combination with the direct view by the remaining half of the camera aperture.

FIG. 13 illustrates another prior art reflecting means for obtaining a single virtual image of half of camera aperture 162 of smart phone 160, for the purpose of obtaining stereoscopic imaging in combination with the remaining half of camera aperture. Knife-edge mirror 164 is positioned close to camera aperture 162 and reflects the light path of half of camera aperture 162 toward mirror 166, where it is further reflected toward aerial image 108. Mirrors 164 and 166 create virtual image 168 of half of the camera aperture 162. This virtual image 168 provides an "offset" field of view, which, in combination with the "direct" field of view from the un-occluded half of camera aperture 162, allows the capturing of the two side-by-side stereoscopic images on the display screen of smart phone 160 that are necessary for stereoscopic viewing. A disadvantage of this technique is that virtual image 168 and the un-occluded portion of camera aperture 162 are at different distances from aerial image 108, resulting in different sized side-by-side stereoscopic images.

Figure 14:
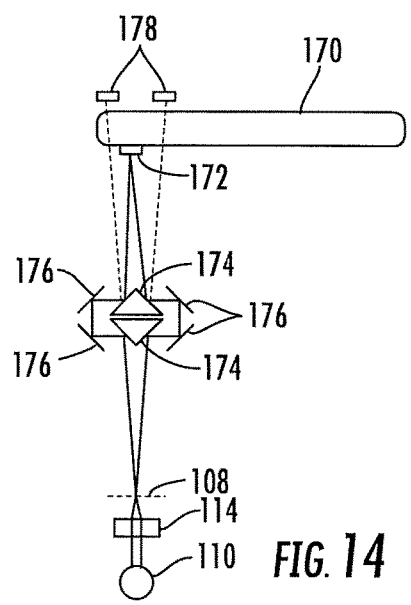
FIG. 14 illustrates an embodiment of the present invention using reflecting means to produce side-by-side aerial images.

FIG. 14 illustrates an embodiment of the present invention using reflecting means to produce side-by-side, aerial images of camera aperture 172 of smart phone 170. Two reflecting knife-edge prisms are positioned as shown in FIG. 14 in combination with four mirrors 176 to produce aerial images 178 of camera aperture 172. The reflecting knife-edge prisms 174 and mirrors 176 are attached to smartphone 180 or otherwise attached to the head-mounted unit in any way known to or conceivable by one of skill in the art in order to produce the side-by-side, aerial images of camera aperture 172. The two aerial images 178, along with the illuminating light source (not shown) are imaged by condensing lens 114 onto the cornea of patient's eye 110, fitting within the pupil of patient's eye 110, for stereoscopic imaging. An advantage of the reflecting apparatus as shown in FIG. 14 is that there is no rotation (tilting) of the stereoscopic images with respect one another.

Figure 15:
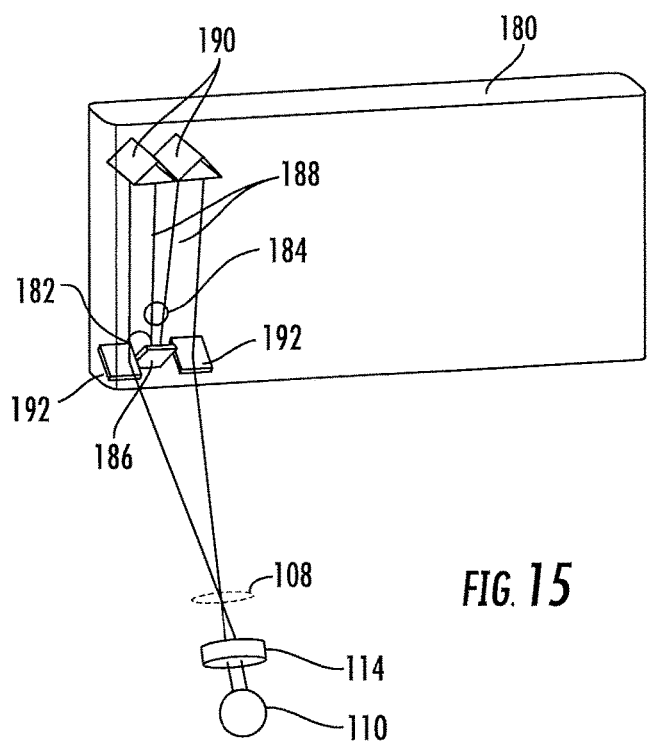
FIG. 15 illustrates an embodiment of the present invention having compact reflecting means for creating two aerial images of the camera aperture of the smart phone.
Figure 16:
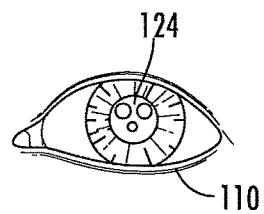
FIG. 16 illustrates a front view of an eye of a subject depicting the placement of the beams of light according to the systems illustrated in FIG. 15.

FIG. 15 illustrates a preferred embodiment of the present invention comprising compact reflecting means for creating two aerial images of camera aperture 182 of smart phone 180. Light source 184 is positioned above camera aperture 182, where it can illuminate condensing lens 114 without being occluded by other apparatus. Positioned below light source 184 is 45° mirror 186. The 45° mirror 186 reflects light paths 188 from camera aperture 182 upward to enter Porro reflecting prisms 190. These light paths are retro-reflected back by the Porro reflecting prisms 190 to 45° mirrors 192, which then reflect the light paths to aerial image 108 of the fundus of patient's eye 110. The virtual images (not shown) of the camera aperture 182 are formed on the far side of smart phone 180, but the bundles of light reaching these virtual images of camera aperture 182 from aerial image 108 are limited by the apertures of 45° mirrors 192. These apertures of 45° mirrors 192, along with light source 184, are imaged onto the cornea of patient's eye 110, and within pupil 124 of patient's eye 110 as illustrated in FIG. 16, affording stereoscopic imaging of the fundus of patient's eye 110. Proper dimensioning and positioning of the elements of the reflecting means in FIG. 15 will ensure proper separation of the virtual images of camera aperture 182 to obtain optimal stereoscopic imaging through pupils of chosen diameters. The 45° mirrors and Porro prisms are attached to smartphone 18 or otherwise positioned on the headmounted device in such a way that the stereoscopic images can be obtained.

An advantage of the reflecting apparatus shown in FIG. 15 is that there is no rotation (tilting) of the stereoscopic images with respect one another. A further advantage of the reflecting apparatus shown in FIG. 15 is that the stereoscopic images of upside-down and reversed aerial image 108 are rotated 180° by the reflecting apparatus, resulting in upright and proper right-to-left stereoscopic images of the fundus of patient's eye 110. But such upright imagery may be unfamiliar to examiners who are used to the rotated imagery of conventional indirect ophthalmoscopy, in which case the side-by-side stereoscopic images can be electronically rotated 180° by smart phone 180, to render the usual indirect ophthalmoscopic imagery. The stereoscopic images may alternatively be routed to separate electro-optical goggles for stereoscopic viewing.

The system can include a dedicated computer application for use in a smartphone or other smart device, as part of the digital imaging system. A special computing device unique to this invention could also be implemented. The computer application can include features to aid in the indirect ophthalmoscopic exam that may include but are not limited to: remote (e.g., blue tooth)-controlled shutter triggering device or a voice-activated shutter, LED brightness adjustment (including background illumination and a flash of light synchronized with each shutter activation), preferential autofocusing in the expected region of the indirect ophthalmoscope's aerial image of the ocular fundus, preferential autofocusing for red/orange color objects, preferential zoom set to the size of the indirect ophthalmoscopic condensing lens held near the subject's eye, automatic blacking out of what is outside the condensing lens, automatic cropping of images/video to what is within the condensing lens, and autoexposure to optimize the brightness of the captured image of the ocular fundus.

Any such computer application will be fixed on a non-transitory computer-readable medium. It should be noted that the computer application is programmed onto a non-transitory computer-readable medium that can be read and executed by any of the computing devices mentioned in this application. The non-transitory computer-readable medium can take any suitable form known to one of skill in the art. The non-transitory computer-readable medium is understood to be any article of manufacture readable by a computer. Such non-transitory computer-readable media include, but are not limited to, magnetic media, such as a floppy disk, flexible disk, hard disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternatively, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application may be transmitted either wired or wirelessly over a network, via the internet, cellular telephone network, or any other suitable data transmission means known to or conceivable by one of skill in the art.

The many features and advantages of the invention are apparent from the detailed specification, and thus it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly all suitable modifications and equivalents may be resorted to, falling within the scope of the invention.

What is claimed is:

1. A system for obtaining side-by-side stereoscopic images of an ocular fundus of a subject, comprising:
    a light source;
    a digital imaging device having an aperture for receiving light reflected from the ocular fundus of the subject;
    optical device for creating side-by-side virtual images of the aperture of the digital imaging device;
    a condensing lens;
    a head-mounting device for head-mounted positioning of the light source, the digital imaging device, and the optical device; and
    wherein the light source, the digital imaging device, and the optical device are positioned to cause the light source and light paths from the side-by-side virtual images to be imaged by the condensing lens to positions separated from one another within a pupil of an eye of the subject, such as to obtain stereoscopic views of the ocular fundus of the subject.

2. The system of claim 1, further comprising:
    binocular electro-optical goggles which electronically to receive the stereoscopic views for stereoscopic viewing by an examiner.

3. The system of claim 1, wherein the optical device comprises a prismatic device.

4. The system of claim 3, wherein the prismatic device comprises a biprism.

5. The system of claim 4, wherein the biprism comprises an achromatic bi prism for reduction of chromatic aberration.

6. The system of claim 1, wherein the optical device comprise a reflecting prism.

7. The system of claim 6, wherein the reflecting prism comprises reflecting surfaces positioned to avoid tilting of the side-by-side stereoscopic images of the ocular fundus with respect to one another.

8. The system of claim 6, wherein the reflecting prism comprises reflecting surfaces chosen from a group consisting of mirrors and internally reflecting prisms.

9. The system of claim 1, wherein the optical device is positioned such that the light source emits a beam of light that is not occluded by the optical device.

10. A system, comprising:
    a digital imaging device having an aperture for receiving light reflected from an ocular fundus of a subject,
        the digital imaging device including a light source;
    an optical device to create side-by-side virtual images of the aperture of the digital imaging device;
    a condensing lens to image the side-by-side virtual images of the aperture of the digital imaging device and the light source onto a cornea of an eye of a patient; and
    a head-mounted device to position the digital imaging device and the optical device so that the side-by-side virtual images of the aperture of the digital imaging device are separated within a pupil of the eye of the subject to obtain stereoscopic views of the ocular fundus of the subject.

11. The system of claim 10, wherein the digital imaging device is a smart phone.

12. The system of claim 10, further comprising:
    binocular electro-optical goggles to receive the stereoscopic views for stereoscopic viewing by an examiner.

13. The system of claim 10, wherein the optical device is a biprism.

14. The system of claim 13, wherein the biprism comprises an achromatic bi prism for reduction of chromatic aberration.

15. The system of claim 10, further comprising:
    bilateral close-up eyepiece lenses to receive the stereoscopic views for stereoscopic viewing by an examiner.

16. The system of claim 10, wherein the optical device comprises a pair of reflecting prisms.

17. A device to image a fundus of a subject, comprising:
    a head-mounted device to be positioned on a head of an examiner,
        the head-mounted device including mounting hardware to receive a smart phone;
    a biprism to create side-by-side virtual images of an imaging aperture of the smart phone, the biprism being mounted onto the head-mounted device with the mounting hardware, the biprism and the smart phone being positioned such that the side-by-side virtual images of the imaging aperture of the smart phone are located adjacent to but not overlapping with the imaging aperture of the smart phone and a light source associated with the smart phone;

a condensing lens to image the side-by-side virtual images of the imaging aperture of the smart phone and the light source of the smart phone onto a cornea of an eye of a patient so that the side-by-side virtual images of the imaging aperture of the smart phone are separated within a pupil of the eye of the subject to obtain stereoscopic views of the fundus of the subject.

18. The device of claim 17, further comprising:

binocular electro-optical goggles to receive the stereoscopic views for stereoscopic viewing by the examiner.

19. The device of claim 17, wherein the biprism comprises an achromatic bi prism for reduction of chromatic aberration.

20. The device of claim 17, further comprising:

bilateral close-up eyepiece lenses to receive the stereoscopic views for stereoscopic viewing by the examiner.

21. The device of claim 17, wherein the biprism is mounted onto the smart phone.

* * * * *

UNITED STATES PATENT AND TRADEMARK OFFICE
CERTIFICATE OF CORRECTION

PATENT NO. : 10,314,486 B2  
APPLICATION NO. : 15/502565  
DATED : June 11, 2019  
INVENTOR(S) : Aaron Wang et al.

Page 1 of 1

It is certified that error appears in the above-identified patent and that said Letters Patent is hereby corrected as shown below:

In the Claims

Claim 2, Column 10, Line 9, "binocular electro-optical goggles which electronically to" should be changed to -- binocular electro-optical goggles to --.

Signed and Sealed this
Ninth Day of June, 2020

Andrei Iancu
*Director of the United States Patent and Trademark Office*